(12) United States Patent
Rusch et al.

(10) Patent No.: US 6,359,191 B1
(45) Date of Patent: Mar. 19, 2002

(54) VAGINAL TAMPON AND PROCESS FOR PRODUCING THE SAME

(75) Inventors: Volker Rusch, Herborn; Kurt Zimmerman, Herbornseelbach; Holger Brunsmann, Herborn; Joachim Bruno Solfronk, Bad Homburg, all of (DE)

(73) Assignee: Symbio Herborn Group GmbH & Co., Herborn-Horbach (DE)

( * ) Notice: Subject to any disclaimer, the term of this patent is extended or adjusted under 35 U.S.C. 154(b) by 0 days.

(21) Appl. No.: 09/402,331

(22) PCT Filed: Apr. 3, 1998

(86) PCT No.: PCT/EP98/01969

§ 371 Date: Oct. 4, 1999

§ 102(e) Date: Oct. 4, 1999

(87) PCT Pub. No.: WO98/44884

PCT Pub. Date: Oct. 15, 1998

(30) Foreign Application Priority Data

Apr. 4, 1997 (DE) .......................................... 197 13 908

(51) Int. Cl.[7] ................................................. A61F 13/15
(52) U.S. Cl. ................... 604/364; 604/385.18; 604/904
(58) Field of Search ....................... 604/385.17, 385.18, 604/604, 364

(56) References Cited

U.S. PATENT DOCUMENTS 6,020,453 A * 2/2000 Larsson et al.
6,187,990 B1 * 2/2001 Runeman et al.

FOREIGN PATENT DOCUMENTS

WO     WO 92/13577    * 8/1992 .................. 604/904

* cited by examiner

*Primary Examiner*—Dennis Ruhl
(74) *Attorney, Agent, or Firm*—Kanesaka & Takeuchi

(57) ABSTRACT

A vaginal tampon contains living lactic acid bacteria (lacto-bacteria) and/or auxiliary substances for treating or regenerating the vaginal flora. The lacto-bacteria and auxiliary substances are enclosed in an air- and water-tight manner between thin layers, which are at least partially dissolved only when the tampon is used. The vaginal tampon releases the lacto-bacteria and/or auxiliary substances.

12 Claims, 5 Drawing Sheets

FIG. 10
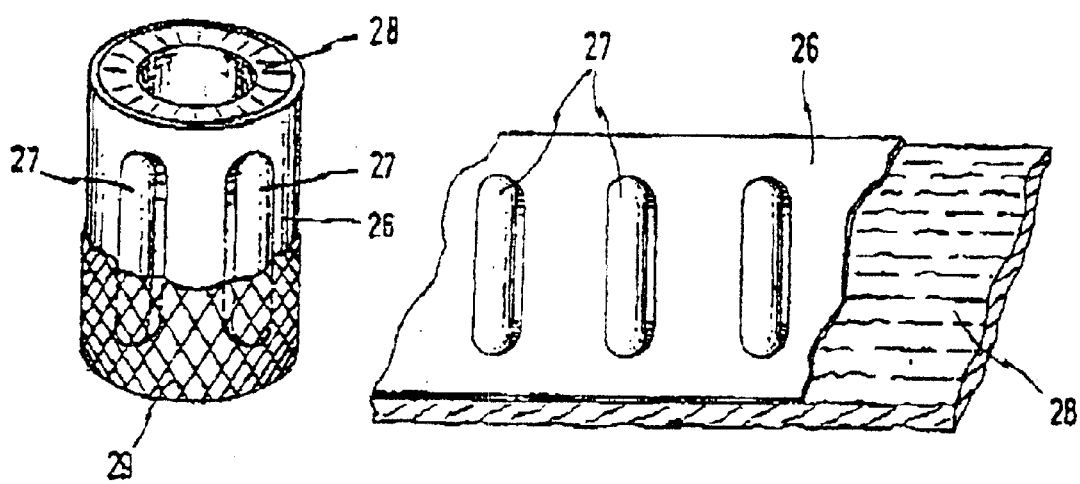
FIG. 11
FIG. 12
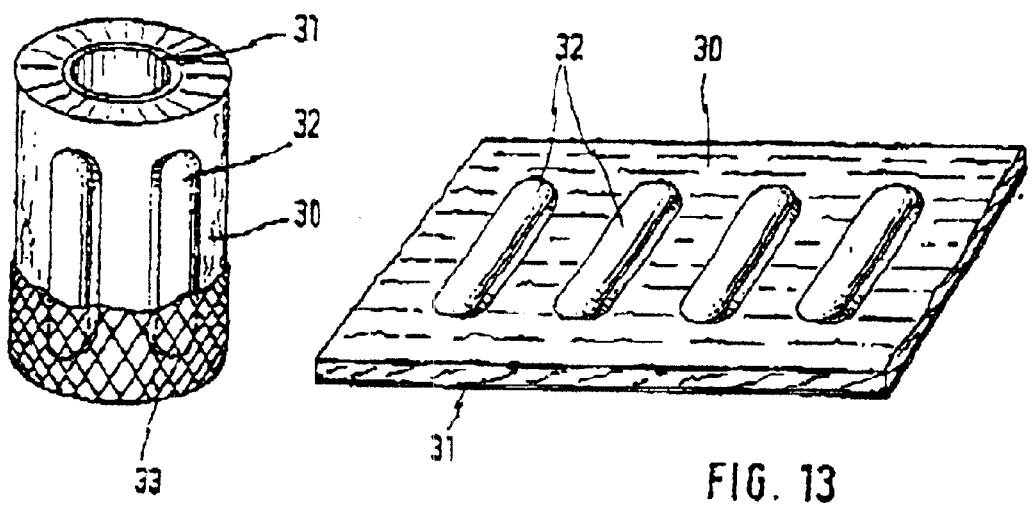
FIG. 13

VAGINAL TAMPON AND PROCESS FOR PRODUCING THE SAME

The invention relates to a vaginal tampon and to a process for producing the same.

The vaginal area of healthy women is a lactic acid environment. A frequent cause of disease in the vaginovulvar area is disturbance of the vaginal flora. A cause or consequence of this is also an increase in pH value. Suppositories for treating the vaginal mucosa are known. A disadvantage of these is that only a relatively small part of the mucous membranes comes into contact with the suppository or with the substance released by it, so that the preventive or therapeutic result is unsatisfactory.

There is therefore a need to provide easy-to-use means for application in the female genital region, which means permit mild care and support of a healthy vaginal flora or also regeneration of a weakened or impoverished vaginal flora and accordingly can to a large extent prevent diseases in the vaginovulvar area.

In this context, the invention is based on the object of making available tampons, and means that can be used like tampons, as carriers of living lactic acid bacteria (lacto-bacteria) and/or substances, which permit simple care and support of a healthy vaginal flora or recovery of said vaginal flora in the context of normal care of the female genital region. Such tampons or the like are referred to below as lacto-tampons and the abovementioned carriers are referred to as lacto-carriers.

The object of the invention is thus to propose a lacto-tampon or the like which is easy to produce and easy to use and which, for the purpose of caring for and supporting a healthy vaginal flora, maintains the closest possible contact with the mucous membranes in the vaginal area and in so doing releases living lacto-bacteria and/or other substances for treating or maintaining the health of the vaginal flora.

According to the invention, the object is achieved by the features of claim 1.

Figure 1:
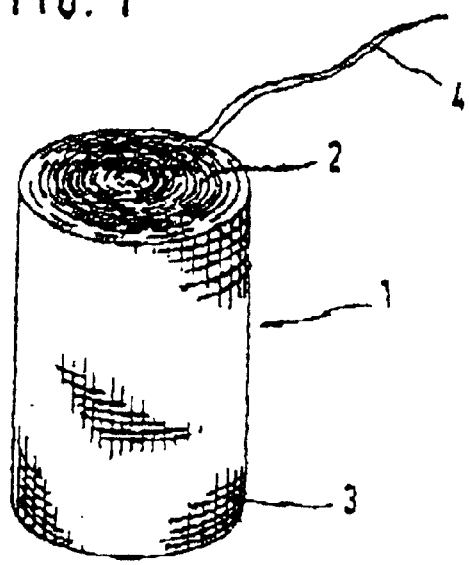
Figure 2:
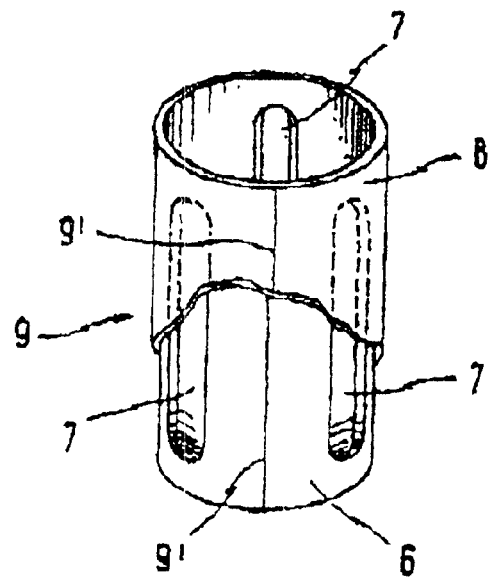
Figure 3:
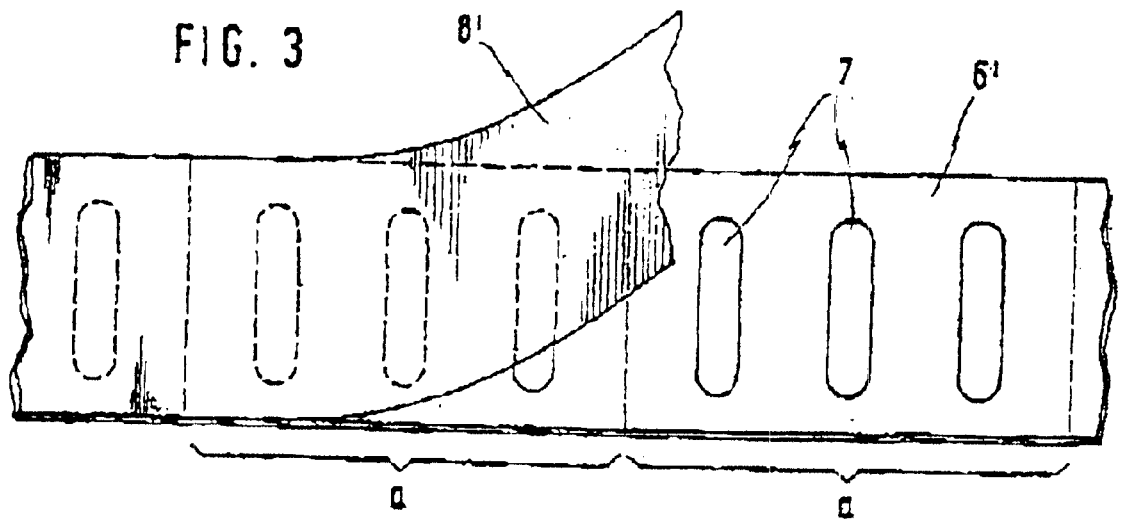
Figure 4:
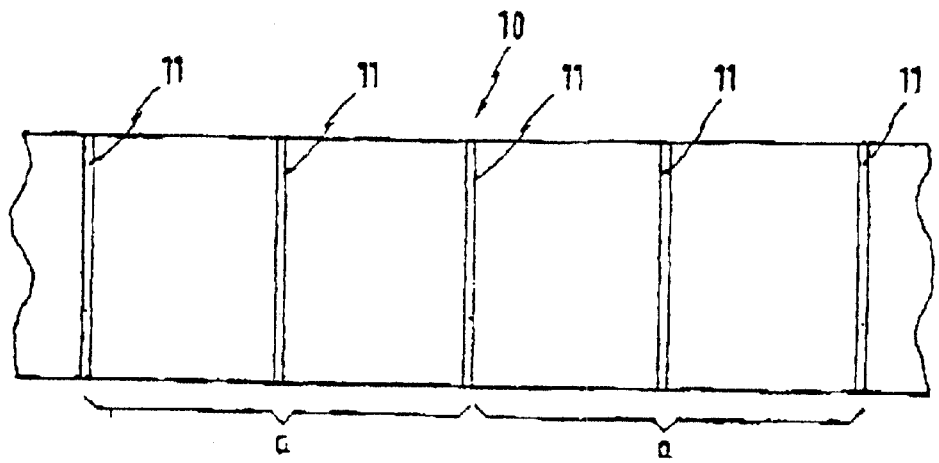
Figure 5:
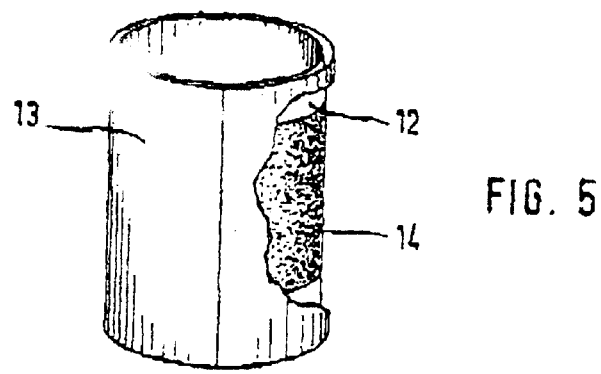
Figure 6:
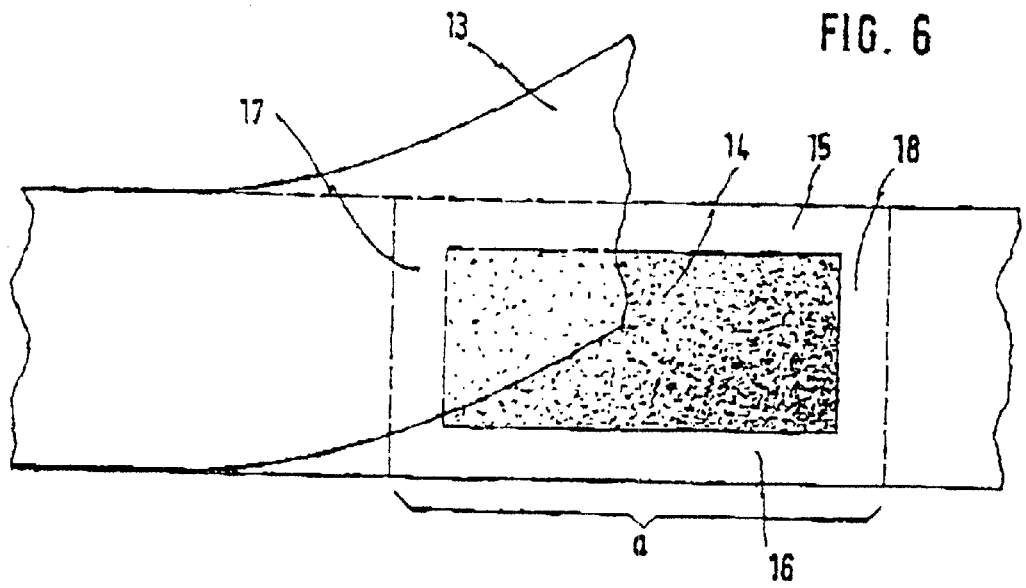
Figure 7:
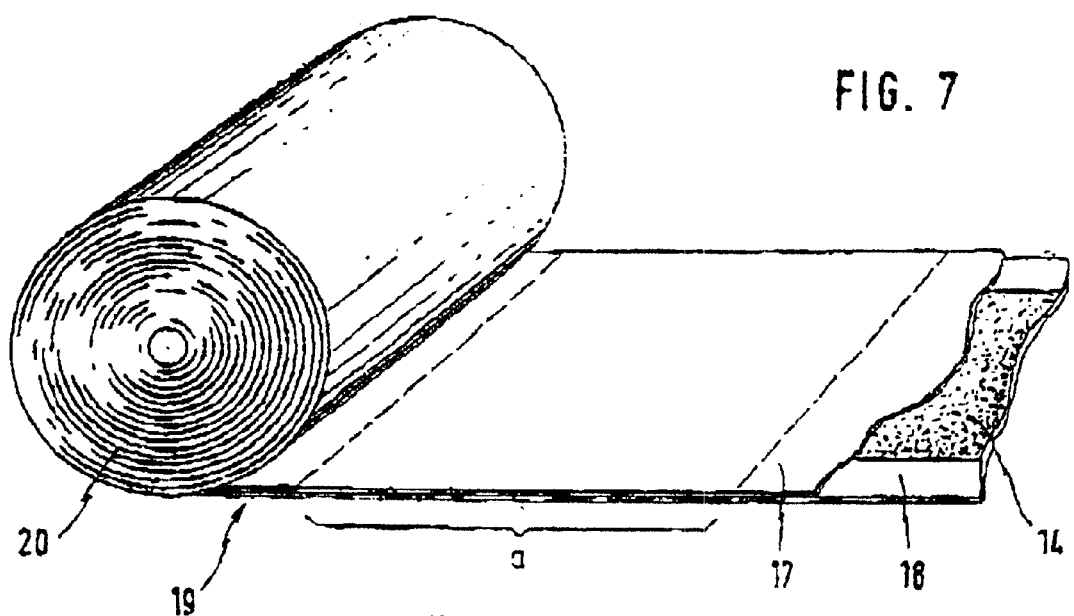
Figure 8:
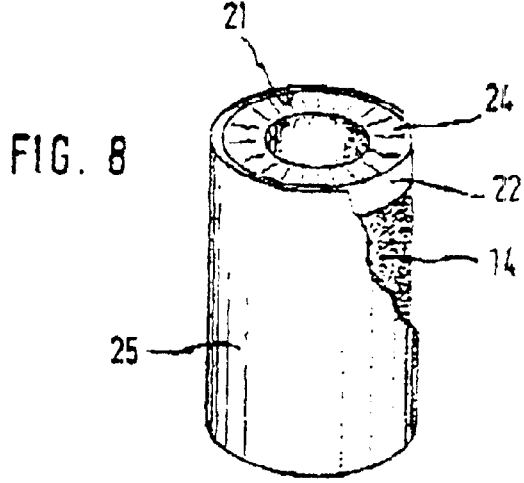
Figure 9:
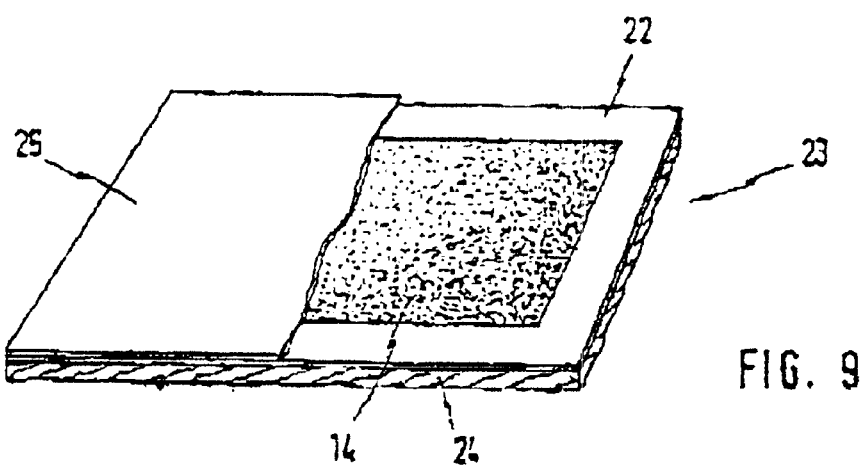
Figure 14:
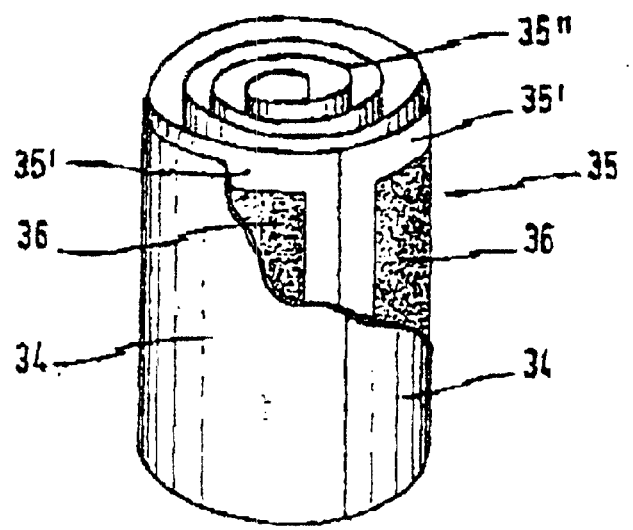
Figure 15:
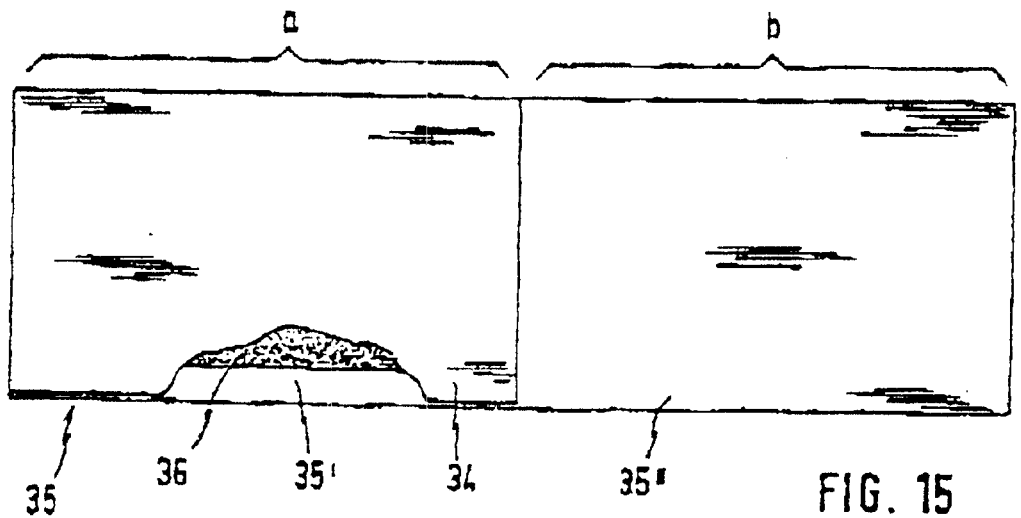
Figure 16:
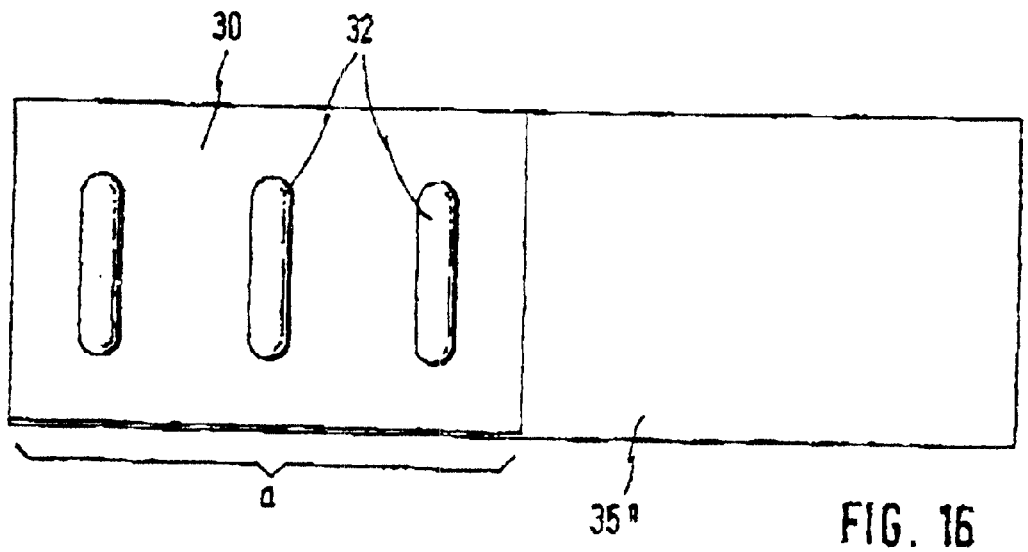

Advantageous embodiments according to the invention will become clear from the features of the subclaims and from the following description. In the associated drawing, illustrative embodiments according to the invention are only shown diagrammatically, and without implying limitation. In said drawing:

FIG. 1 shows a conventional vaginal tampon, in a perspective view,

FIG. 2 shows a lacto-carrier for a tampon according to the invention, likewise in a perspective view, and partially broken open, FIG. 3 shows a phase in the production of the lacto-carrier according to FIG. 2, FIG. 4 shows the inner part of a lacto-carrier for a tampon according to the invention, in a plan view, FIG. 5 shows a further lacto-carrier for a tampon according to the invention, in a perspective view, and partially broken open, FIG. 6 shows a phase in the production of the lacto-carrier according to FIG. 5, FIG. 7 shows a lacto-carrier band wound up into a roll, with a multiplicity of contiguous lacto-carriers each for a tampon according to the invention, FIG. 8 shows a further tampon according to the invention, in a perspective view, and partially broken open, FIG. 9 shows the tampon according to FIG. 8 spread out flat, in a perspective plan view, and partially broken open, FIG. 10 shows yet another tampon according to the invention, in a perspective view, and partially broken open, FIG. 11 shows the tampon according to FIG. 10 spread out flat, in a perspective plan view, and partially broken open, FIG. 12 shows yet another tampon according to the invention, in a perspective view, and partially broken open, FIG. 13 shows the tampon according to FIG. 12 spread out flat, in a perspective plan view, FIG. 14 shows yet another tampon according to the invention in a perspective view, and partially broken open, FIG. 15 shows the tampon according to FIG. 14 spread out flat, in a plan view and partially broken open, FIG. 16 shows a variant of the tampon according to FIGS. 14 and 15, likewise in a plan view.

FIG. 1 is a perspective representation of a conventional vaginal tampon 1 for absorbing the menstrual fluid. The tampon comprises a highly compressed cotton web 2, which is rolled up in a spiral and tightly pleated in the longitudinal direction, inside a tightly pleated nonwoven fabric, lattice tulle or the like which is designated by 3 and which, for holding the rolled-up cotton web 2, is designed as a tubular sleeve of the tampon 1. A string 4 is attached to the cotton web for the purpose of withdrawing the tampon after it has been used.

FIG. 2 shows a lacto-carrier as an annular or cylindrical body, which can, for example, enclose a conventional tampon according to FIG. 1 with or without its pleated nonwoven sleeve.

According to the invention, the lacto-carrier according to FIG. 2 comprises two thin, tightly superposed and firmly adhering layers 6 and 8 of water-soluble gelatin or similar polypeptides, as used, for example, for medication capsules. These and comparable layers are referred to below, without any limitation, as gelatin layers.

In the example shown, the inner gelatin layer contains a plurality of chamber-like depressions 7 which are arranged uniformly at a distance from one another around the circumference of the lacto-carrier and extend in the longitudinal direction of the lacto-carrier. In the example shown, three identical elongate depressions 7 are provided. The number of depressions and their configuration does not limit the invention. The elongate arrangement in the longitudinal direction of the lacto-carrier is chosen so as to be able to convert the latter easily from a flat, band-like section to a cylindrical or annular shape and to facilitate insertion of the tampon. At least one depression 7 is provided.

The inner gelatin layer 6 is covered by the plane outer gelatin layer 8. The two layers are connected firmly to one another in an air-tight and water-tight manner so that the individual chamber-like depressions 7 are each tightly sealed off.

A granular lyophilisate of lactic acid bacteria (lacto-lyophilisate) is introduced into at least one depression 7. If desired, it is also possible for all the depressions to be filled with the lacto-lyophilisate. It can be advantageous for at least one of the chambers 7 to be filled with an auxiliary substance, which for example promotes the growth of the released lacto-bacteria and their contact with the vaginal mucosa and/or has a positive influence on the natural vaginal flora present. These substances can be, for example, nutrient media for the lacto-bacteria, lactic acid for supporting the naturally present vaginal flora, and inulin and oligofructoses. The auxiliary substance, also as a mixture, can also be present in lyophilic or lipophilic, gelatin-insoluble, liquid form.

The two gelatin layers 6 and 8 forming a ring or cylinder as carriers of lacto-lyophilisate and/or the aforementioned auxiliary substances can form a sleeve 9 of a cotton tampon or can also be used without the latter with adequate stiffness, as a hollow body in the manner of a tampon.

The outer-lying gelatin layer 8 advantageously has a considerably high or ready solubility in the moist environment of the vagina, in order for the lacto-lyophilisate to be released as soon as possible after insertion of the tampon, while the inner gelatin layer 6 has a comparatively low solubility or can also be essentially insoluble during the period of use. Here, it can be advantageous for the layer thickness of the outer gelatin layer 8 to be chosen thinner than that of the inner gelatin layer 6, so that the lower solubility of the inner gelatin layer 6 is also controlled by the layer thickness alone, for example.

The reason for the different solubilities lies in the fact that the absorption power of the tampon cotton of conventional tampons (if the lacto-carrier is used as tampon sleeve for tampon cotton) has to be turned off to a large extent during the period of action of the introduced lacto-bacteria so as not to impede or to make it difficult for the lacto-bacteria to make contact with the mucous membranes.

If no tampon cotton is used, the inner gelatin layer serves as a support frame for the lacto-carrier which can be used in the manner of a tampon. In this case, the inner gelatin layer can also be insoluble. In combination with a small string, as in the case of a conventional tampon, the inner gelatin layer which has not been dissolved or which has been incompletely dissolved can be withdrawn from the vagina after use.

If the lacto-carrier is used as a sleeve of a conventional cotton tampon for example, it can be advantageous to provide the inner gelatin layer 6 of the lacto-carrier with a relatively high water solubility at at least one narrow location, so that during use, this location acts as a break point after dissolving and in this way a radial expansion of the tampon cotton is made possible after taking up moisture. The absorption power of the tampon cotton then remains substantially screened off radially to the outside except for the relatively small area of the break point in the inner gelatin layer 6.

According to the invention, it can also be advantageous to once again substantially release the absorption effect of the tampon cotton after a selected treatment time. For this purpose, the full dissolubility of the inner gelatin layer is set correspondingly as regards the time. The lacto-tampon then acts, during an initial time, as a means for recovering or maintaining the health of the vaginal flora and subsequently, in a conventional manner, for taking up the menstrual fluid. The lacto-tampon according to the invention can therefore also be used a short time before the onset of menstruation.

FIG. 3 shows, only in principle, how a two-layer carrier for lacto-lyophilisate and/or the aforementioned auxiliary substances can be produced.

In an endless band-shaped gelatin strip 6', the depressions 7 into which lacto-lyophilisate and/or the auxiliary substances are separately filled are successively made using a filling mechanism (not shown). A second endless band-shaped gelatin strip 8' is then tightly attached on the gelatin strip 6', the individual depressions 7 with the filled-in substances being tightly sealed off in each case.

In order to bring the lacto-carriers into the annular or cylindrical shape according to FIG. 2, sections "a" are separated off from the double-wall gelatin strip 6', 8' and are brought into the annular or cylindrical shape according to FIG. 2, the ends of one section being bonded together or welded together to form a joint or seam 9.

The gelatin layer 6 having the depressions 7 does not necessarily have to be the inner layer, and the covering gelatin layer 8 does not necessarily have to be the outer layer, as is shown in the lacto-carrier in FIG. 2. The gelatin layer having the depressions can also lie outside and the covering gelatin layer 8 can lie on the inside, in which case the aforementioned solubilities are also correspondingly changed around.

FIG. 4 shows an inner gelatin strip 10 from which, in accordance with FIG. 3, sections "a" are separated off in each case to form a lacto-carrier. The gelatin strip 10 has a succession of transverse strips 11 spaced apart from one another and made of a gelatin material having a relatively higher solubility than the rest of the gelatin material.

If a double-wall lacto-carrier is produced using a section "a" of the gelatin strip 10, during use it breaks open after dissolution of the narrow gelatin strip 11 and thus permits radial expansion of the tampon cotton in the center of the lacto-carrier, in which case the absorption effect remains essentially blocked by the undissolved section "a" of the gelatin strip 10.

In the example shown using an inner gelatin layer according to FIG. 2, produced from the gelatin strip according to FIG. 4, the inner gelatin layer breaks into two half shells after two gelatin strips 11 have dissolved, which half shells block the absorption effect of the tampon cotton to the outside at least during a predetermined length of time.

FIG. 5 shows a variant of a hollow lacto-carrier according to the invention comprising an inner gelatin layer 12 and an outer gelatin layer 13. In the present case, neither the inner nor the outer gelatin layer has depressions. Instead, lyophilisate, for example, of a granular material is applied in a narrow strip 14 centrally onto one of the two flat gelatin layers 12 or 13, as is shown in FIG. 6. The respective other gelatin layer serves as a plane cover layer. For tightly sealing the lyophilisate strip 14 between the two gelatin layers 12 and 13, the layers are tightly bonded or welded to one another on their longitudinal lower and upper edges 15 and 16 and on transverse dividing locations 17 and 18 at a distance "a". The lacto-carrier according to FIG. 5 is then formed from a double-wall gelatin section of length "a", the outer-lying gelatin layer once again having a comparatively high water solubility and the inner gelatin layer having a comparatively low water solubiltiy or being insoluble, depending on whether the lacto-carrier is being used without or with a central cotton tampon. In the latter case, the inner gelatin layer can also be configured according to FIG. 4.

It can also be advantageous to produce an endless double-walled gelatin strip comprising a plurality of successive sections "a", each for a lacto-carrier, for example according to FIG. 2 or 5, or for further lacto-carriers or lacto-tampons described below, in an endless web 19 and to roll the latter up into a supply roll 20, as is indicated diagrammatically in FIG. 7. To produce a lacto-carrier, a section "a" having the length of the circumference of a lacto-carrier is separated from the supply roll and the lacto-carrier or lacto-tampon is brought from this into a cylindrical or annular shape.

It can also be advantageous to arrange a thin cotton layer 24 on the inner side 21 of the inner gelatin layer 22 of the lacto-carrier 23 according to FIG. 8. The outer gelatin layer 25 serves to cover the lacto-lyophilisate 14 which, for example according to FIG. 6, is applied in a strip shape on the inner gelatin layer 22.

FIG. 9 shows the lacto-carrier 23 with the inner cotton layer 24 acording to FIG. 8 spread out in a perspective view from above, and partially broken open.

The thin inner cotton layer 24 has virtually no real absorption effect and serves mainly to increase the stability of the lacto-carrier. It is clear that the above solution is also suitable for the illustrative embodiments of the invention which have been described above. In this way the lacto-carrier becomes a lacto-tampon with a low cotton proportion, which has an insignificant absorption effect.

FIG. 10 shows a further lacto-tampon according to the invention, which is rolled out flat in FIG. 11.

Gelatin capsules 27 which, for example, contain lacto-lyophilisate and/or auxiliary substances of the type described above are securely arranged at a distance from one another in succession on the upper side of a single gelatin layer 26. On the underside of the gelatin layer 26 there is a relatively thin cotton layer 28. However, this cotton layer can also be omitted if the remaining lacto-carrier has sufficient stability to be able to be used in the manner of a tampon.

The individual gelatin capsules 27 here replace the outer gelatin layer within the meaning of the above illustrative embodiments.

It can be advantageous for the lacto-tampon according to the invention in FIG. 10 to be enclosed in a coarse-mesh, tubular lattice tulle sleeve or the like, in the same way as in conventional tampons. The coarse mesh is advantageous so as not to impede the contact between the lacto-bacteria and the mucous membranes.

FIG. 12 shows yet another lacto-tampon according to the invention, which is rolled out flat in FIG. 13.

The lacto-tampon here comprises a narrow cotton layer 30 practically without absorption effect. The cotton layer is carried by a sparingly soluble or insoluble gelatin layer 31. Readily soluble gelatin capsules 32, which for example contain lacto-lyophilisate and/or auxiliary substances, are arranged at a distance from one another on the upper side of the cotton layer 30.

To stabilize the lacto-tampon with the outer-lying cotton layer 30 and the gelatin capsules 32 carried by it on its outside and the inner gelatin layer 31, the latter is situated inside a very wide-mesh lattice tulle sleeve 33. The thin cotton layer 30 serves here, during use, as an incubation site for the lacto-bacteria released by the dissolved capsules, from which site they come into contact with the mucous membranes.

Finally, FIG. 14 shows another lacto-tampon according to the invention which is rolled out flat in FIG. 15.

Lyophilisate 36 is tightly enclosed, for example in the manner according to FIG. 6, between an outer readily soluble gelatin layer 34 and an inner sparingly soluble or insoluble gelatin layer 35. The outer gelatin layer 34 extends over the whole outer circumference "a" of the lacto-tampon and, with the section 35' of the more sparingly soluble gelatin layer 35 covered by it, forms a closed cylindrical or annular body. The inner, optionally insoluble gelatin layer 35 protrudes beyond the outer gelatin layer 34 with an adjoining section 35" by a chosen distance "b". The gelatin section "b" is rolled up in a spiral with selected radial prestressing to form the tampon, as is shown diagrammatically in FIG. 14 in perspective view. Only when the outer gelatin layer 34 has dissolved during use does the radial prestressing of the inner gelatin section 35" come to act on the section 35'.

The thickness and the elastic stressing of the inner gelatin layer 35 can be chosen such that the radially outwardly directed prestressing can be chosen at the desired extent so that after the outer readily soluble gelatin layer 34 has dissolved during use, an intensive contact between the released lacto-bacteria and the mucous membranes of the vagina is ensured.

It is clear that the illustrative embodiments mentioned above can correspondingly be equipped with an inner gelatin spiral, according to the invention, of the above type.

FIG. 16 shows another variant in which, instead of the outer gelatin layer 34, an outer cotton layer 30 corresponding to FIGS. 12, 13 is present and carries, for example, gelatin capsules 32 for lacto-lyophilisate and/or auxiliary substances, in which case the cotton layer with the gelatin capsules is held in a wide-mesh lattice tulle 33 according to FIG. 12.

The lacto-bacteria can be selected from the group comprising *Lactobacillus acidophilus, Lactobacillus casei, Bifidobacterium bifidum, Streptococcus lactis* and *Lactobacillus reuteri*. A mixture of several of these bacteria is advantageously used.

The invention is not limited to the illustrative embodiments, which can, within the context of the invention, prompt the skilled person to further modifications without difficulty.

What is claimed is:

1. A vaginal tampon comprising:

a cylindrical lacto-carrier including an outer cylindrical gelatin layer, an inner cylindrical gelatin layer having a solubility smaller than that of said outer layer, and at least one living lactic acid bacteria enclosed between said outer and inner layers; and a vaginal cotton tampon enclosed in a space surrounded by said inner layer of said lacto-carrier.

2. A vaginal tampon comprising:

a cylindrical lacto-carrier including an outer cylindrical gelatin layer, an inner cylindrical gelatin layer having a solubility smaller than that of said outer layer, and at least one living lactic acid bacteria enclosed between said outer and inner layers; and a cotton layer arranged on an inner surface of said inner layer of said lacto-carrier.

3. A vaginal tampon comprising:

a cylindrical lacto-carrier including a cylindrical gelatin layer, at least one gelatin capsule having a solubility larger than that of said cylindrical layer and arranged on an outer surface of said cylindrical layer, and at least one living lactic acid bacteria enclosed in said gelatin capsule;

an outer lattice tulle sleeve enclosing said cylindrical lacto-carrier; and a vaginal cotton tampon enclosed in a space surrounded by said cylindrical layer of said lacto-carrier.

4. A vaginal tampon comprising:

a cylindrical lacto-carrier including a cylindrical gelatin layer, at least one gelatin capsule having a solubility larger than that of said cylindrical layer and arranged on an outer surface of said cylindrical layer, and at least one living lactic acid bacteria enclosed in said gelatin capsule;

an outer lattice tulle sleeve enclosing said cylindrical lacto-carrier; and a cotton layer arranged on an inner surface of said cylindrical layer of said lacto-carrier.

5. A vaginal tampon according to claim 1 or 2, wherein one of said inner and outer layers has at least one depression for accommodating said lactic acid bacteria.

6. A vaginal tampon according to claim 1 or 2, wherein said lacto-carrier further includes at least one auxiliary substance selected from lactic acid, inulin or oligofructoses, said auxiliary substance being enclosed between said inner and outer layers.

7. A vaginal tampon according to claim 1 or 2, wherein one of said inner and outer layers has at least one depression for accommodating said lactic acid bacteria, and said lacto-carrier further includes at least one auxiliary substance selected from lactic acid, inulin or oligofluctoses, said auxiliary substance being enclosed between said inner and outer layers.

8. A vaginal tampon according to claim 1 or 2, wherein said inner cylindrical layer has at least one narrow longitudinal strip region having therein a solubility larger than that of a region of said inner cylindrical layer that is not comprised within said strip region.

9. A vaginal tampon according to claim 1 or 2, wherein said inner layer has a free end section, which is rolled up as a central spiral.

10. A vaginal tampon according to claim 1, 2, 3 or 4, wherein said living lactic acid bacteria is selected from the group consisting of *Lactobacillus acidophilus, Lactobacillus casei, Bifidobacterium bifidum, Streptococcus lactis,* and *Lactobacillus reuteri.*

11. A vaginal tampon according to claim 3 or 4, wherein said lacto-carrier further includes at least one auxiliary substance selected from lactic acid, inulin or oligofluctoses, said auxiliary substance being enclosed in said at least one of said gelatin capsules.

12. A vaginal tampon according to claim 3 or 4, wherein said cylindrical layer has at least one narrow longitudinal strip region having therein a solubility larger than that of a region of said cylindrical layer that is not comprised within said strip region.

* * * * *